United States Patent
Robison et al.

(10) Patent No.: US 6,401,529 B1
(45) Date of Patent: Jun. 11, 2002

(54) APPARATUS AND METHOD FOR DETERMINING CONSTITUENT COMPOSITION OF A PRODUCED FLUID

(75) Inventors: Clark E. Robison, Tomball; Charles R. Williams, Carrollton; Neal G. Skinner, Lewisville, all of TX (US)

(73) Assignee: Halliburton Energy Services, Inc., Dallas, TX (US)

( * ) Notice: Subject to any disclaimer, the term of this patent is extended or adjusted under 35 U.S.C. 154(b) by 5 days.

(21) Appl. No.: 09/672,529

(22) Filed: Sep. 28, 2000

(51) Int. Cl.[7] .......................... G01N 3/22; G01N 11/00; G01N 33/28; F21B 47/10; G02F 1/74
(52) U.S. Cl. ................ 73/152.19; 73/152.18; 73/61.43; 73/64.55; 73/863.21
(58) Field of Search .............. 73/152.19, 152.18, 73/152.55, 61.41, 61.43, 61.44, 64.55, 863.21

(56) References Cited

U.S. PATENT DOCUMENTS

| | | | | |
|---|---|---|---|---|
| 2,295,437 A | * | 9/1942 | Thompson | 73/152.19 |
| 3,611,799 A | * | 10/1971 | Davis | 73/152.55 |
| 3,721,121 A | * | 3/1973 | Fierfort | 73/155 |
| 3,826,133 A | * | 7/1974 | Nicolas et al. | 73/152 |
| 3,990,304 A | * | 11/1976 | Roesner | 73/151 |
| 5,033,288 A | * | 7/1991 | Castel | 73/61.1 R |
| 5,090,238 A | * | 2/1992 | Jones | 73/155 |
| 5,092,988 A | * | 3/1992 | Womack, III et al. | 210/85 |
| 5,211,842 A | * | 5/1993 | Tuss et al. | 210/87 |
| 5,417,107 A | * | 5/1995 | Biencourt et al. | 73/61.44 |
| 5,616,856 A | * | 4/1997 | Castel | 73/61.45 |
| 5,698,791 A | * | 12/1997 | Lemaire | 73/861.04 |
| 6,212,948 B1 | * | 4/2001 | Ekdahl et al. | 73/152.18 |
| 6,272,906 B1 | * | 8/2001 | Fleury et al. | 73/64.55 |

\* cited by examiner

*Primary Examiner*—Hezron Williams
*Assistant Examiner*—David J. Wiggins
(74) *Attorney, Agent, or Firm*—William M. Imwalle; Lawrence R. Youst

(57) ABSTRACT

A downhole apparatus (100) for determining the constituent composition of a produced fluid is disclosed. The apparatus (100) includes a vessel (106) having an interior chamber (108) that receives and contains a sample of the produced fluid. In the interior chamber (108), the sample of the produced fluid is allowed to separate into its constituents. A gauge (200) having an array of transmitter elements (E1–E17) and an array of corresponding receiver elements (R1–R17) disposed oppositely of one another on the vessel (106), is used to transmit and receive energy waves that propagate through the sample of the produced fluid. The receiver elements (R1–R17) detect changes in absorption or scattering of the energy waves transmitted from the corresponding transmitter element (E1–E17) caused by the constituent of the sample of the produced fluid through which that energy wave propagated. Based upon these changes in the energy waves, the level of an interface between the constituents is identified such that the constituent composition of the produced fluid may be determined.

30 Claims, 6 Drawing Sheets

APPARATUS AND METHOD FOR DETERMINING CONSTITUENT COMPOSITION OF A PRODUCED FLUID

TECHNICAL FIELD OF THE INVENTION

The present invention relates in general to an apparatus and method for analyzing production fluids from a subterranean formation and, in particular, to an apparatus and method for determining the constituent composition of the produced fluids with a downhole fluid analyzing device that communicates correlating data to the well surface.

BACKGROUND OF THE INVENTION

One aspect of reservoir management includes maximizing the daily production of hydrocarbons from a particular producing interval. When multiple zones are commingled in a single tubing string and the combined effluent from all of the zones is flowed to the surface, it is difficult to discriminate the contribution from each interval. Accordingly, it is desirable to gather and monitor the gross flowrate from each producing interval and to determine the constituent volumetric flowrates of oil, water and gas. Another aspect of reservoir management is maximizing the total recoverable reserves from the reservoir. This typically requires more detailed knowledge of the constituent rates from each interval which may be used to determine the most optimum flow regime. For example, such data can be used to select the optimum flowrates for each of the producing zones as well as the appropriate hydrocarbon to water ratios to, among other things, prevent coning.

In the past, one method of obtaining data relating to the constituents of production fluids from a particular producing interval was through sampling. This procedure typically required lowering wireline tools downhole after the production flow was ceased, isolating the zone of interest, reinitiating the fluid flow from that zone, obtaining the. production fluid sample, ceasing the flow and then retrieving the sample. This procedure would then be repeated for the other zones of interest. It has been found, however, that the costs associated with this procedure are high due to well downtime and the associated loss of production revenue.

Another method of obtaining fluid flow data has been through the use of permanent downhole gauges which obtain production fluid data without the need for shutting in production. Such permanently installed completion systems have incorporated multi-drop downhole data acquisition and control systems which include an array of downhole sensors spaced throughout a well. Such sensors have been used to monitor pressure and temperature characteristics. It has been found, however, that such sensors are relatively ineffective in identifying the constituent volumetric flowrates of the production fluids.

Therefore, a need has arisen for an apparatus and method that provide information relating to the daily production of hydrocarbons from a particular producing interval. A need has also arisen for such an apparatus and method that provide detailed information relating to the constituent rates from each interval. Additionally, a need has arisen for such an apparatus and method that provide this information without having to cease production.

SUMMARY OF THE INVENTION

The present invention disclosed herein comprises an apparatus and method that provide information relating to the daily production of hydrocarbons from a particular producing interval. Specifically, the apparatus and method of the present invention provide detailed information relating to the constituent rates from each interval. Using the apparatus and method of the present invention, this information is obtained without having to cease production.

The apparatus of the present invention comprises a vessel having an interior chamber that is in selective communication with a stream of fluids produced from a subterranean formation. A flow control device associated with the apparatus is used to selectively permit and prevent the produced fluid from entering and exiting the interior chamber.

For example, the flow control device may have an open position, wherein the produced fluid flows through the interior chamber of the apparatus and a closed position, wherein the produced fluid in the interior chamber is contained as a sample.

Once such a sample is obtained, the sample is allowed to separate within the interior chamber into its constituents using, for example, gravitational separation. In a typical sample of produced fluids, the constituents may include gas, oil and water. Due to the differences in the specific gravity of these constituents, the gas migrates to the top of the interior chamber and the water migrates to the bottom of the interior chamber with the oil positioned therebetween. As such, a gas/oil boundary forms between the gas and the oil. Likewise, an oil/water boundary forms between the oil and the water.

A gauge attached to the vessel is used to identify the location of these boundaries which allows for the determination of the constituent volumetrics of the produced fluid. The gauge may include an array of transmitter elements and an array of corresponding receiver elements that are disposed oppositely of one another on the vessel. Each of the transmitter elements transmits an energy wave through the sample of the produced fluid that is received by the corresponding receiver element. The receiver elements detect changes in the energy waves caused by the constituent of the sample of the produced fluid through which that energy wave propagated.

For example, if the energy waves propagated through the sample are light waves, the gas constituent will absorb a portion of the light energy, the oil constituent will be substantially opaque to the light energy and the water constituent will be substantially transparent to the light energy. As such, the locations of the gas/oil boundary and the oil/water boundary may be identified. Once the locations of the boundaries are identified, this information may be sent to a data acquisition system on the surface such that the constituent composition of the sample of the produced fluid may be calculated.

In the method of the present invention, the constituent composition of a produced fluid is determined by disposing a fluid analyzing device having an interior chamber downhole, selectively communicating the interior chamber with a stream of the produced fluid, collecting a sample of the produced fluid in the interior chamber, allowing the produced fluid to separate into constituents and identifying the level of an interface between the constituents with a gauge.

BRIEF DESCRIPTION OF THE DRAWINGS

For a more complete understanding of the present invention, including its features and advantages, reference is now made to the detailed description of the invention, taken in conjunction with the accompanying drawings of which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the invention.

Figure 1:
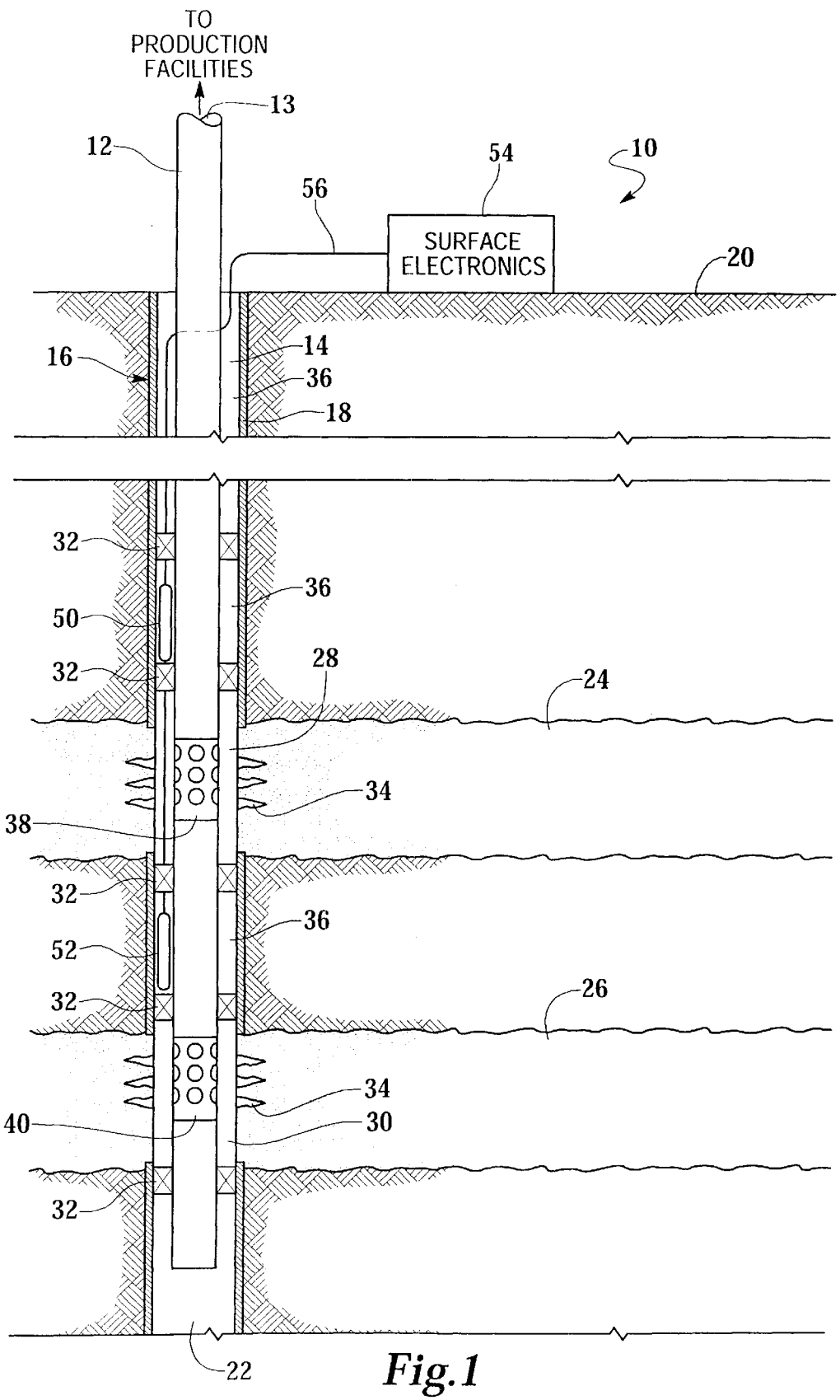
FIG. 1 is a schematic view of a well having multiple production zones each having a fluid analyzing device of the present invention positioned for analyzing production fluids.

Referring now to the drawings, and more particularly to FIG. 1, shown is a simplified well production structure 10 having a tubing string 12 lowered into a wellbore 14 of a well 16. For clarity, the wellhead structures commonly associated with production devices are not shown. Nevertheless, the present invention described below may be deployed in more extensive and complex production well structures having multiple producing formations. Further, although the present invention is shown deployed in a land-based well, the present invention can also be deployed in sea-based wells.

The wellbore 14 is lined with a casing string 18 to stabilize the soil and formations that define the wellbore 14. The wellbore 14 extends from the surface 20 of the well 16 to a lower interior zone 22 through a formation 24 and a formation 26. Isolation packers 32 are deployed along the wellbore 14 adjacent formations 24 and 26 to define fluid production zones 28 and 30. Isolation packers 32 isolate formations 24 and 26 from infiltration by fluids or other materials that may be in well annulus 36.

Perforations 34 are made into formations 24 and 26 to promote fluid flow from formations 24 and 26 into production zones 28 and 30, respectively. Perforated tubing 38 and 40 is provided adjacent formations 24 and 26 to allow fluid communication between formations 24 and 26 and an inner bore 13 of tubing string 12. As will be appreciated, formations 24 and 26 each contain fluids to be produced by well production structure 10.

Disposed within wellbore 14 are fluid analyzing devices 50 and 52. Fluid analyzing devices 50 and 52 monitor production fluid characteristics and fluid trends over time as will be explained in greater detail below. Each of the fluid analyzing devices 50 and 52 are substantially similar. Fluid analyzing device 50 monitors. the fluid at a position above production zone 28 while fluid analyzing device 52 monitors the fluid at a position above production zone 30. It should be apparent to those skilled in the art that the use of directional terms such as above, below, upper, lower, upward, downward and the like are used in relation to the illustrative embodiments as they are depicted in the figures, the upward direction being toward the top of the corresponding figure and the downward direction being toward the bottom of the corresponding figure.

Fluid analyzing devices 50 and 52 are coupled to tubing string 12, and are in fluid communication with inner bore 13. As such, fluid analyzing devices 50 and 52 retrieve samples of the production fluid from inner bore 13 of the tubing string 12. These production fluid samples may be taken on an interval basis, periodic or random, or on demand to generate a trend-history of the production fluid.

Fluid analyzing devices 50 and 52 are coupled to surface electronics 54 through a communications and power cable 56. Through cable 56, fluid analyzing devices 50 and 52 receive electric and/or optical power from the surface and transmit electronic and/or optical data regarding downhole conditions to the surface for processing by surface electronics 54. Surface electronics 54 include a data acquisition system for collecting and storing information. Furthermore, a microprocessor may be used to perform an analysis of the data to determine trends or to calculate certain parameters that are useful in reservoir management.

Cable 56 may be a complex data and power path cable embedded in tubing string 12 and having electronic controls incorporated throughout for separate control of several downhole tools, or may be a single cable accompanying each of the fluid analyzing devices 50 and 52. An example of such a power path is provided by U.S. Pat. No. 5,547,029, issued Aug. 20, 1996, to Rubbo et al., which is incorporated herein by reference.

Other transmission mediums can be used to provide the communications and power requirements for fluid analyzing devices 50 and 52. For example, a conventional rechargeable battery pack can be used to provide downhole power, while communication capacities can be provided by a signal receiver/transmitter and control circuit. The signal receiver and control circuit may receive telemetry signals from a surface control system (not shown) located at surface 20. An example of a signal receiver and control circuit is provided in U.S. Pat. No. 5,555,945, issued Sep. 17, 1996, to Schultz et al, which is incorporated herein by reference.

Fluid analyzing devices 50 and 52 are configured to sample the fluid in tubing 12 adjacent to fluid analyzing devices 50 and 52. By compiling the data from each fluid analyzing devices 50 and 52 and subtracting the signals, the constituent contribution from each formation 24 and 26 is determined.

Figure 2:
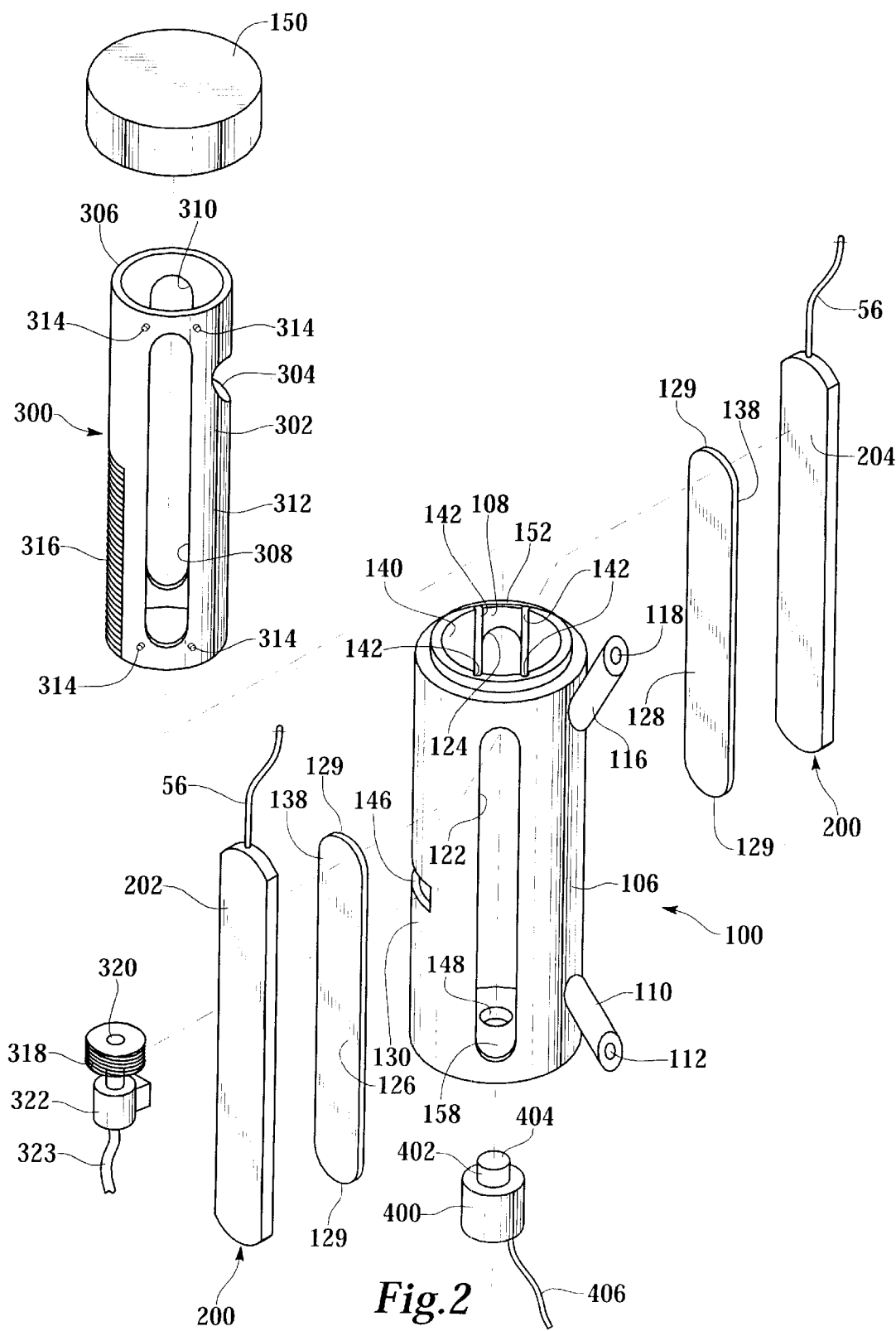
FIG. 2 is an exploded view of a fluid analyzing device of the present invention.

In FIG. 2, shown is an exploded view of a fluid analyzing device 100. Fluid analyzing device: 100 has a vessel 106 with a constituent gauge 200 for sensing the constituent levels of a sampled fluid contained in vessel 106. The sampled fluid is retrieved and contained in vessel 106 by actuating a flow control device 300 which controls the flow of fluids through fluid analyzing device 100.

Vessel 106 has an interior chamber 108 with a substantially circular cross-sectional area. Vessel 106 has an inlet port member 110 near the bottom of vessel 106 that defines an interior passage 112 therethrough. Vessel 106 also has an outlet port member 116 spaced apart from the inlet port member 110 near the top to vessel 106 that defines interior passage 118 therethrough. Interior passage 112, interior passage 118 and interior chamber 108 are in fluid communication and establish an internal flow path such that a sample of a production fluid from inner bore 13 of tubing string 12 (see FIG. 1) can flow through vessel 106.

Vessel 106 also defines oppositely disposed sight window slots 122 and 124 that receive sight windows 126 and 128, respectively. Sight windows 126 and 128 each have curved end portions 129 that are matingly accepted in slots 122 and 124 to ease stresses exerted against sight windows 126 and 128 during transport down wellbore 14. Also, each of the sight windows 126 and 128 are preferably curved about respective longitudinal axes to substantially adapt to the outer surface of vessel 106.

Constituent gauge 200 is secured to vessel 106 adjacent sight windows 126 and 128 to measure the constituent level of a fluid sample contained in vessel 106. The constituent level measurements are conducted by detecting a transition from one constituent to another, the boundary being designated by the constituent transition. Constituent gauge 200 receives power from and transmits electronic data relating to the constituent boundaries of the sample to surface electronics 54 through cable 56 (see FIG. 1).

Constituent gauge 200 includes a receiver unit 202 and a transmission unit 204 that are coupled such that signals may pass therebetween to determine the level of the constituents in the fluid sample by distortion of the signals through the fluid sample. That is, with transmission unit 204 transmitting substantially similar signals through vessel 106 along the overall length of sight window 128, the difference between constituents is delectable by comparing the signals received by receiver unit 202 over the length of the sight window 126.

The signals transmitted between receiver unit 202 and transmission unit 204 may be optical, electronic, electromagnetic, radioactive, acoustic, or other suitable signal type. An optical system may be most preferred due to reliability and simplicity of the components. One suitable optical system is commercially available from Clairex Technologies, Inc., of Plano, Tex.

The structure of vessel 106 and flow control device 300 accommodates the signal transmission of constituent gauge 200. Sight windows 126 and 128 are made of a material that is substantially transparent to the signal used to sense the constituent levels of fluid within vessel 106. For example, for optical signals, sight windows 126 and 128 are substantially transparent to the light wave frequencies that photonically couple receiver unit 202 and transmission unit 204.

For the downhole transmission and reception of optical signals in the light wave frequency-band, a preferable sight window material is quartz. Preferably, receiver unit 202 and transmission unit 204 each have a concave inner surface with an area greater than or equal to an area of an outer surface 138 of sight windows 126 and 128. Similarly, the concave inner surfaces of receiver unit 202 and transmission unit 204 complement the outer surface of vessel 106.

It should be noted by those skilled in the art that with some gauging devices using, for example, acoustic or radiation gauging techniques, sight windows may not be required because the materials of vessel 106 are substantially transparent to such signals.

Flow control device 300 is received in vessel 106 such that in an open position, a sample of formation fluid can be retrieved in interior chamber 108 by opening inlet port member 110 and outlet port member 116. Likewise, in a closed position, flow control device 300 obstructs inlet port member 110 and outlet port member 116 such that a fluid sample is contained in vessel 106. While contained in vessel 106, the fluid sample is separated or stratified into constituents using gravity separation techniques.

Flow control device 300 has an inner sleeve 302 that defines an inner sleeve flow passage 304 spaced apart from an upper lip 306. Flow passage 304 is positioned to substantially align with outlet port member 116 when inner sleeve 302 is in the open position. Inner sleeve 302 also defines inner sleeve slot 308 and inner sleeve slot 310. Slots 308 and 310 are sized to substantially approximate the size of sight window slots 122 and 124 of vessel 106 to minimize interference with the test signal communications to receiver unit 202 from transmission unit 204.

Extending from an outer surface 312 of inner sleeve 302 are alignment pins 314. At least two alignment pins 314 are received in the alignment channels 142 defined on an inner surface 140 of vessel 106. This alignment configuration restricts movement of inner sleeve 302 with respect to vessel 106 to only longitudinal movement.

Flow control device. 300 has an actuator including a gear-rack assembly 316 to drive sleeve 302 from the first position to the second position. A mating gear 318 engages the gears of gear-rack assembly 316 to drive inner sleeve 302 between open and closed positions. The mating gear 318 is rotated by a shaft 320 extending from an electric motor 322. The electric motor 322 receives electrical power through a cable 323 which may be coupled to surface electronics 54 via cable 56 (see FIG. 1). Electric motor 322 is fixed to the outer surface 130 of vessel 106. The mating gear 318 extends through a gear slot 146, defined in vessel 106, to engage gear-rack assembly 316.

With the control flow device 300 positioned in vessel 106, a removable cap 150 is threadingly received on the mating threads 152 at the top of vessel 106. Removable cap 150 contains inner sleeve 302 within the vessel 106.

Also shown in FIG. 2, is a transducer 400 to measure a physical characteristic of the fluid sample contained in vessel 106. Transducer 400 is a device that converts environmental stimuli into a relational electrical output signal. Examples of a downhole environmental stimuli are heat, strain, pressure and the like. Transducer 400 is coupled through a cable 406 to a power source and control source such as surface electronics 54 (see FIG. 1).

Transducer 400 has a threaded stem 402 that is received in a threaded aperture 148 defined in the bottom surface 158 of vessel 106. When so positioned, the sensor element 404 is in communication with a fluid sample contained in interior chamber 108.

Figure 3:
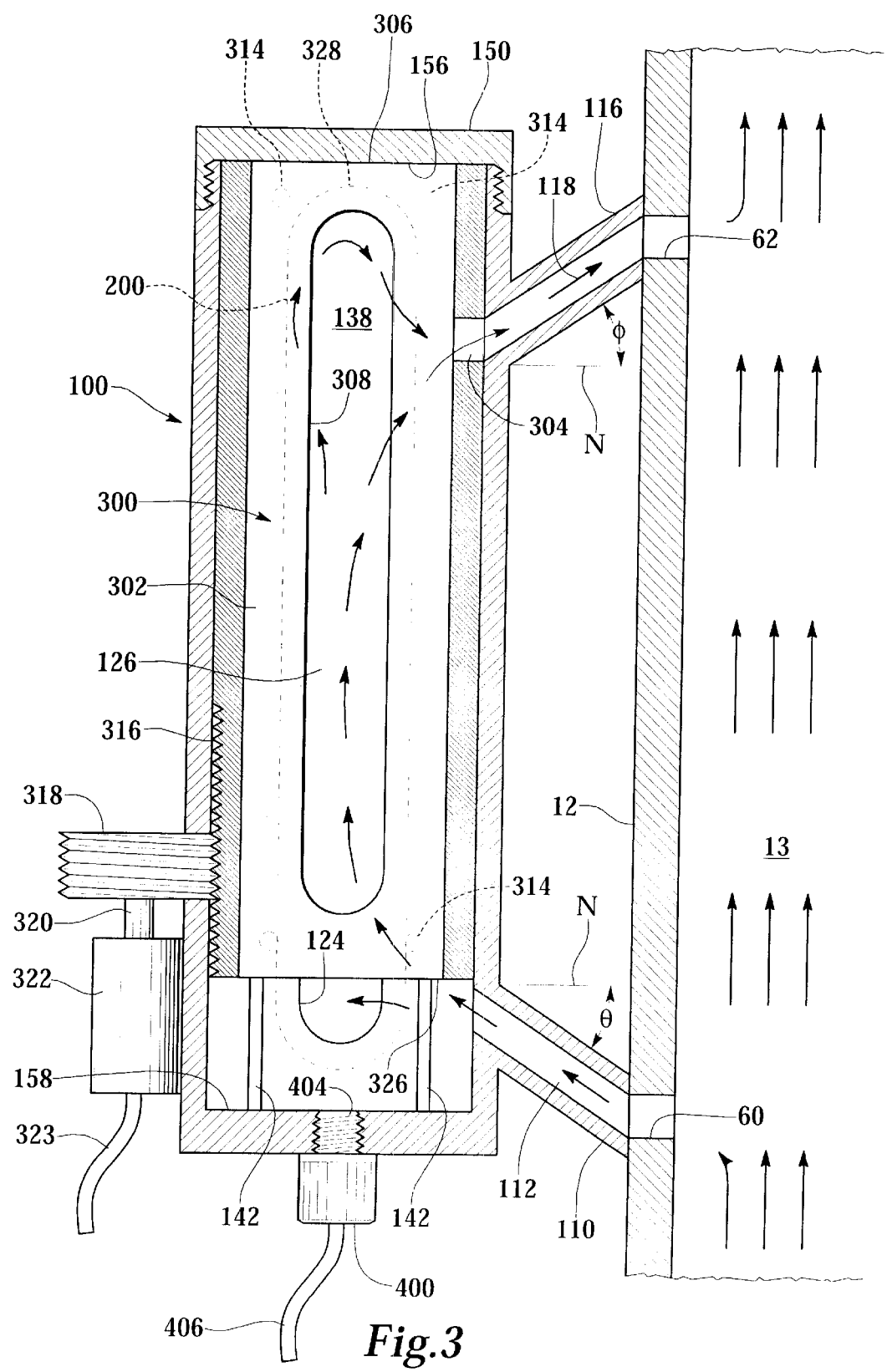
FIG. 3 is aside cross-sectional view of a fluid analyzing device of the present invention in the open position.

Referring now to FIG. 3, therein is depicted a cross-sectional view of fluid analyzing device 100 in the open position where a portion of the fluid flow in inner bore 13 of tubing string 12 flows through fluid analyzing device 100. The general fluid flow through fluid analyzing device 100 is depicted by a series of arrows.

As seen in FIG. 3 there is a deviation of interior passage 112 and interior passage 118 with respect to the vessel 106. Interior passage 112 deviates by an angle θ with respect to normal line N of vessel 106. Interior passage 118 deviates by an angle φ with respect to normal line N of vessel 106. The angles θ and φ are selected to allow fluids from inner bore 13 to flow through fluid analyzing device 100 at a flow rate sufficient to flush previous samples from interior chamber 108. Preferable, angles θ and φ are about 45 degrees.

In the open position, upper lip 306 of inner sleeve 302 is adjacent an inner surface 156 of the removable cap 150. Inner sleeve flow passage 304 is substantially aligned with interior passage 118 of outlet port member 116. A lower lip 326 of inner sleeve 302 is adjacent and above interior passage 112 of inlet port member 110 such that interior passage 112 is unobstructed by inner sleeve 302. As shown, movement of inner sleeve 302 is restricted to the longitudinal direction by alignment pins 314 and alignment channels 142. Interior passages 112 and 118 are coupled to the fluid flow passing through ports 60 and 62, respectively, in tubing string 12.

As shown, fluid analyzing device 100 is secured sufficiently near tubing string 12 to ease the travel of fluid analyzing device 100 downhole while minimizing damage. Further ruggedness and durability can be added by placing reinforcing structures about inlet port member 110 and outlet port member 116.

Figure 4:
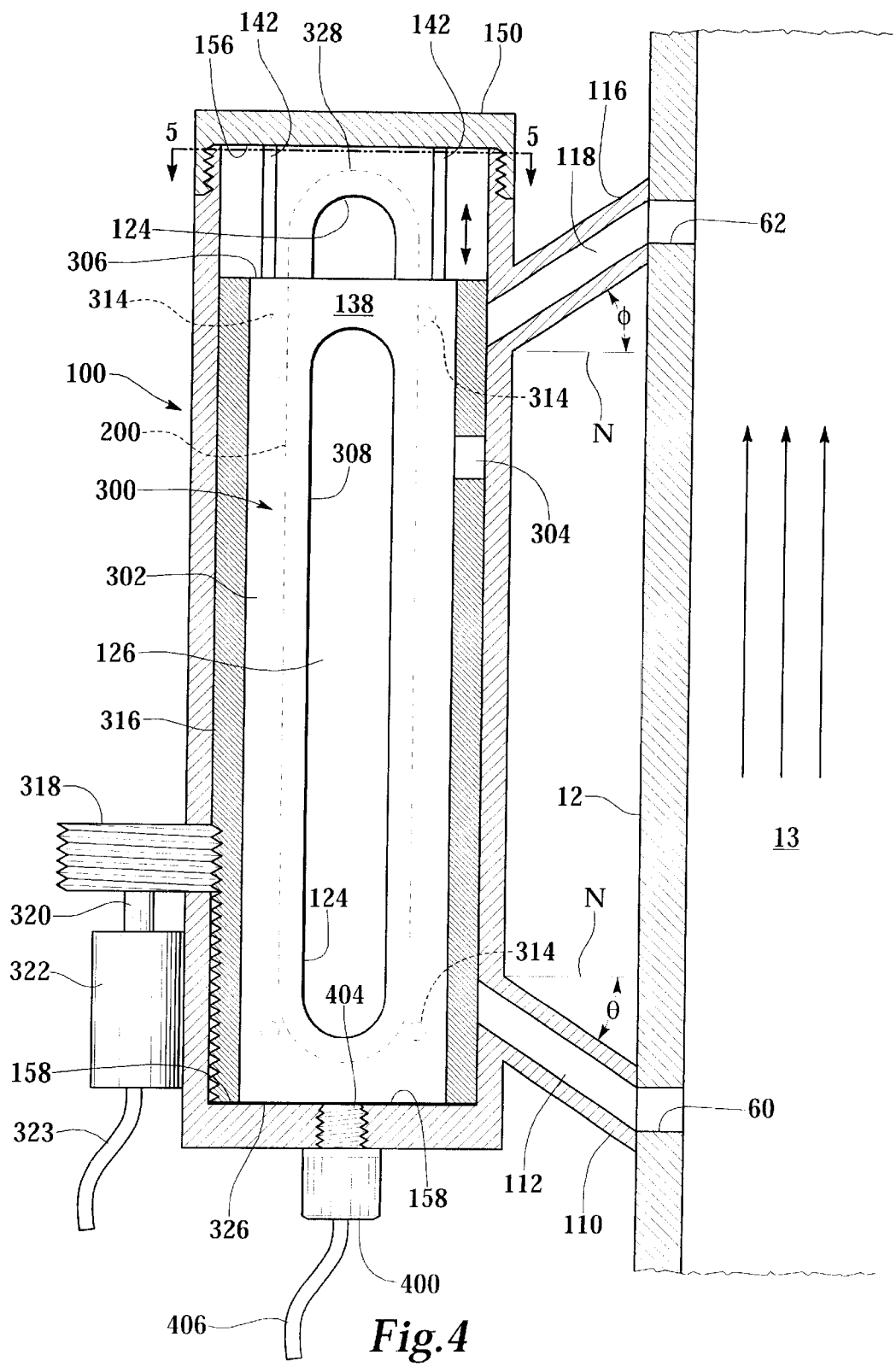
FIG. 4 is a side cross-sectional view of a fluid analyzing device of the present invention in the closed position.

In FIG. 4, fluid analyzing device 100 is shown in the closed position where a portion of the fluid flow from tubing string 12 is contained as a sample. In the closed position, the lower lip 326 of inner sleeve 302 is adjacent the bottom surface 158 of vessel 106. Inner sleeve 302 flow passage 304 is longitudinally shifted downward such that inner sleeve 302 obstructs the interior passage 112 of inlet port member 110. Similarly, the inner sleeve flow passage 304 is no longer aligned with interior passage 118 of outlet port member 116.

A reinforcing structure 328 is between upper lip 306 of inner sleeve 302 and the upper end 330 of the inner sleeve slot 310. Reinforcing structure 328 is preferably used to provide strength and durability to inner sleeve 302 when fluid analyzing device 100 encounters extreme downhole pressures or abrasive forces.

Figure 5:
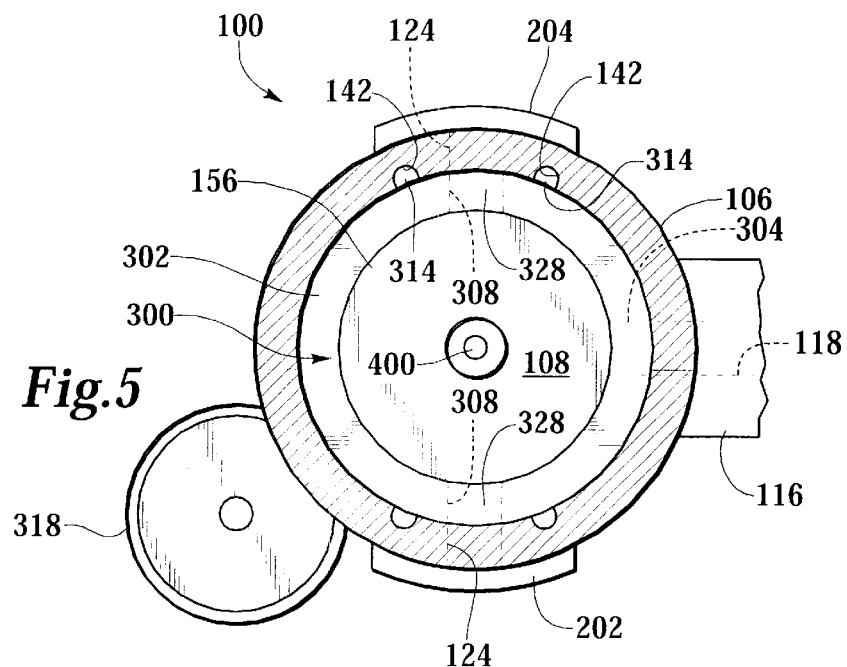
FIG. 5 is a top cross-sectional view of the fluid analyzing device of FIG. 4 taken along lines 5—5.

Referring now to FIG. 5, shown is a top cross-sectional view of device 100 taken along line 5—5 in FIG. 4. Inner sleeve 302 of flow control device 300 is contained within vessel 106 in a substantially concentric fashion to limit lateral movement of inner sleeve 302 with respect to vessel 106. Also shown is the engagement of alignment pins 314 with alignment channels 142 to restrict rotational movement of inner sleeve 302 with respect to vessel 106. Thus, the rotational alignment of inner sleeve flow passage 304 is maintained with interior passage 118 of outlet port member 116.

In the illustrated embodiment, receiver unit 202 and transmission unit 204 of constituent gauge 200 are oppositely disposed on vessel 106. Orienting constituent gauge 200 at this distance is preferable because a greater distortion effect to the transmitted signal is caused by the contained fluid. In addition, transducer 400 is centrally positioned within vessel 106.

Figure 6:
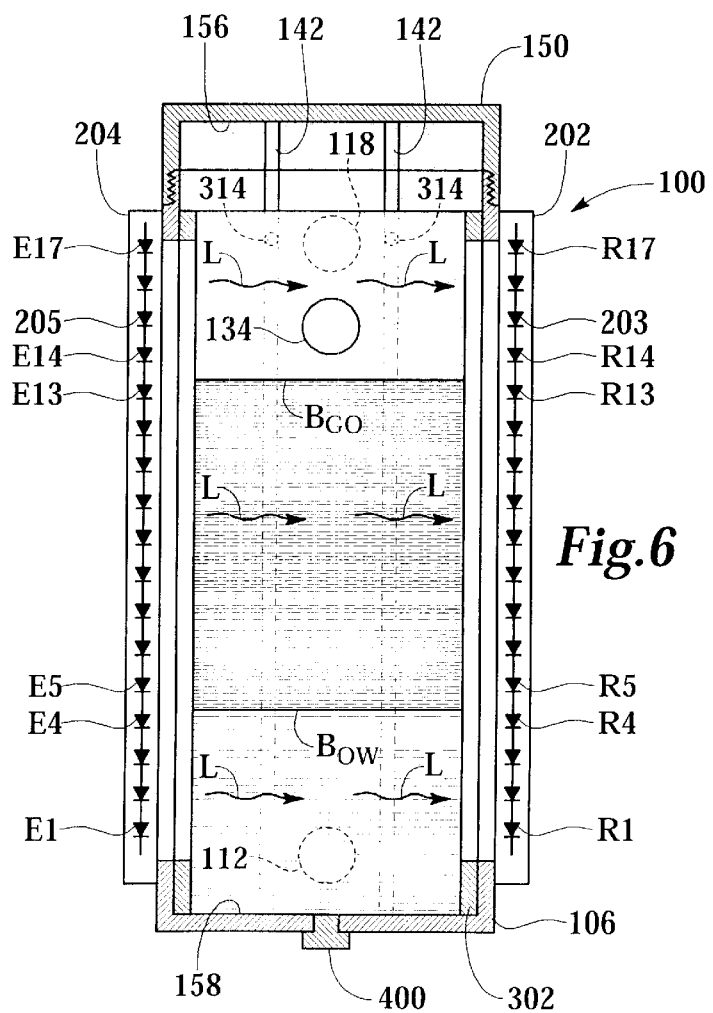
FIG. 6 is a side cross-sectional view of a fluid analyzing device of the present invention in the closed position and containing a production fluid sample separated into its constituents.

In FIG. 6, a side cross-sectional view of fluid analyzing device 100 is shown with a production fluid sample contained therein that has separated or stratified into its constituents. In the illustrated embodiment, there are three constituents represented which are gas, oil and water. Each of the constituents has different density characteristics that allow for gravitational separation. Also shown are constituent boundaries $B_{GO}$ and $B_{OW}$. Boundary $B_{GO}$ exists between the gas and the oil constituents. Boundary $B_{OW}$ exists between the oil and the water constituents.

The boundaries of the sampled production fluids are generated by separating or stratifying the sample into its constituent parts. When initially sampled, the fluid is known as "crude," which is an unprocessed fluid from a formation. The crude includes dissimilar or diverse constituents such as oil, gas and water as well as other liquids and solids that are commingled in a suspension.

In operation, a sample of the production fluid is retrieved by placing inner sleeve 302 in the open position (see FIG. 3). The production fluid is allowed to flow through fluid analyzing device 100 for a time sufficient to allow a fresh crude sample to cycle into interior chamber 108. After a sufficient time has passed, for example about 20 minutes under a 2,000 psi flow, inner sleeve 302 is placed in the closed position, obstructing inlet port member 110 and outlet port member 116 (see FIG. 4). The sampled fluid is now contained in vessel 106.

The constituent representation of the sampled crude fluid is generated by gravity separation techniques. That is, because each of the constituents has a different density, each constituent naturally tends to separate or stratify to its to level over time. For example, water is typically the densest constituent while the second densest is oil and gas is the least dense.

For well monitoring, a sufficient time duration to allow the sampled fluid to separate into the gas, oil and water constituents with boundaries $B_{GO}$ and $B_{OW}$ may be about twenty-four hours. The separation time period may vary from formation-to-formation due to the individual characteristics of the produced fluid. Typically, the greater the separation period, the greater the separation. The amount of separation may be-observed using fluid analyzing device 100 to determine when separation is complete.

After sufficient time has passed such that the sampled fluid has separated into constituent portions, transmission unit 204 transmits signals, such as light waves L having an amplitude A through the separated fluid from transmitter elements E1–E17 spaced along the length of the transmission unit 204.

Transmission unit 204 has a photo-transmission array 205. Photo-transmission array 205 may include light-emitting diodes ("LEDs"), semiconductor lasers, lamps, thermoluminescent materials, radioisotope-activated phosphors, optical fibers extending from a source at the surface or other light- wave transmission circuits having a quantifiable photonic output to that is transmittable to receiver unit 202 for detection.

Receiver unit 202 receives the light waves L transmitted from transmission unit 204 through the separated fluid. At receiver unit 202, the sampled fluid has distorted the originally transmitted light wave L such that originally transmitted sinusoidal has a distorted amplitude of A'.

Receiver unit 202 has a photo-detection array 203 including receiver elements R1–R17. The photo-detection array 203 may include photodetectors, light-dependent resistors ("LDRs"), photo-diodes or other light-sensitive circuits having a quantifiable electrical or optical output that represents the input signal that can be transmitted to surface electronics 54 (FIG. 1) for analysis and recording for determination of formation trends.

A comparison between the electrical outputs of each receiver element R1–R17 in array 203 indicates the transition between the constituent layers such that the locations of boundaries $B_{GO}$ and $B_{OW}$ may be identified. Such formation monitoring may be performed by repeatedly calculating the constituent volumes using fluid analyzing device 100. These calculations generate a production trend for the constituent volumes in the production fluid within tubing string 12 which is adjacent to fluid analyzing device 100. The calculations can occur on an interval basis (either periodic or random) or on demand by appropriate electronic control of the flow control device 300.

The volume of each of the constituents can be determined based upon the location of boundaries $B_{GO}$ and $B_{OW}$. In the example of FIG. 6, the boundary $B_{GO}$ is shown to occur between elements E4 and E5. The boundary $B_{OW}$ is shown to occur between elements E13 and E14. Thus, the volume of water is determined based upon the location of boundary $B_{OW}$ relative to bottom surface 158, the volume of oil is determined by the distance between boundaries $B_{OW}$ and $B_{GO}$ and the volume of gas is determined by the location of $B_{GO}$ relative to upper surface 156 or by subtraction. Generally, the greater the number of elements in the arrays, the greater the precision in determining the location of the boundaries between the stratified constituents.

The volume of the constituents on a percentage basis is calculated as:

$$\% \text{ Water} = \frac{V_{water}}{V_{total}} \quad \% \text{ Gas} = \frac{V_{gas}}{V_{total}} \quad \% \text{ Oil} = \frac{V_{oil}}{V_{total}}$$

Further sample characteristic analysis can be performed using transducer 400. Transducer 400 can be selected to measure the pressure of the sampled fluid within interior chamber 108. This pressure measurement can be, for example, used to determine the volume of gas in solution in the oil.

Figure 7:
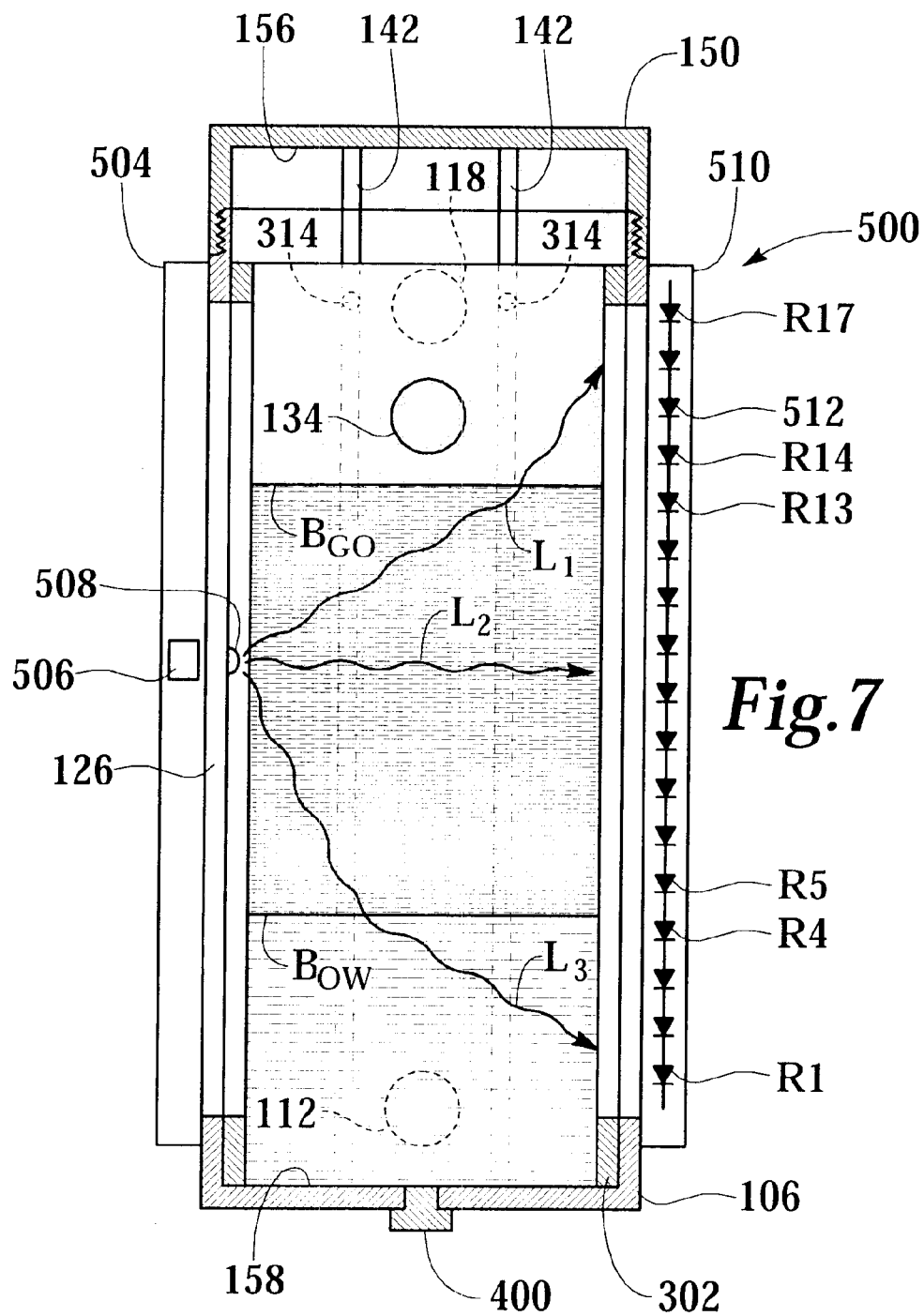
FIG. 7 is a side cross-sectional view of a fluid analyzing device of the present invention in the closed position and containing a production fluid sample separated into its constituents.

In FIG. 7, a side cross-sectional view of fluid analyzing device 500 is shown with a production fluid sample contained therein that has separated or stratified into its constituents. In the illustrated embodiment, there are three constituents represented which are gas, oil and water. Also shown are constituent boundaries $B_{GO}$ and $B_{OW}$. Boundary $B_{GO}$ exists between the gas and the oil constituents. Boundary $B_{OW}$ exists between the oil and the water constituents.

In operation, a sample of the production fluid is retrieved by placing inner sleeve 302 in the open position (see FIG. 3). The production fluid is allowed to flow through fluid analyzing device 500 for a time sufficient to allow a fresh crude sample to cycle into interior chamber 108. After a sufficient time has passed, inner sleeve 302 is placed in the closed position, obstructing inlet port member 110 and outlet port member 116 (see FIG. 4). The sampled fluid is now contained in vessel 106 and allowed to separate into the constituent portions.

After sufficient time has passed such that the sampled fluid has separated into constituent portions, transmission unit 504 transmits an optical signal, such as light, through lens 508 which may be disposed interiorly on site window 126 as pictured or may be formed as part of site window 126 or as a stand alone device. Lens 508 spreads the light into a plurality light waves, such as light waves $L_1$, $L_2$ and $L_3$ which propagate through the separated fluid.

Receiver unit 510 receives the light waves spread by lens 508 and transmitted through the separated fluid. At receiver unit 510, the sampled fluid has distorted the originally transmitted light waves. Specifically, some of the light waves will be distorted not only by the fluid through which they propagate but also by the fluid interface through which they travel. For example, light wave $L_1$ travels through oil, boundary $B_{GO}$ and gas. Light wave $L_1$ will be distorted due to absorption by the oil and the gas as well as the difference between the refractive index of oil, $n_O$, and the refractive index of gas, $n_G$, as light wave $L_1$ travels through boundary $B_{GO}$. Likewise, light wave $L_3$ will be distorted due to absorption by the oil and the water as well as the difference between the refractive index of oil, $n_o$, and the refractive index of water, $n_W$, as light wave $L_3$ travels through boundary $B_{OW}$. These refractive indices may be determined by analysis of a prior sample.

Receiver unit 510 has a photo-detection array 512 including receiver elements R1–R17. The photo-detection array 512 may include photodetectors, LDRs, photo-diodes or other light-sensitive circuits having a quantifiable electrical or optical output that represents the input signal that can be transmitted to surface electronics 54 (FIG. 1) for analysis and recording for determination of formation trends.

Based upon a comparison between the electrical outputs of each receiver element R1–R17 in array 512, the locations of boundaries $B_{GO}$ and $B_{OW}$ may be determined. In the example of FIG. 7, the boundary $B_{GO}$ is shown to occur between elements E4 and E5 and the boundary Bow is shown to occur between elements E13 and E14. As above, the volume of each of the constituents can be determined based upon the location of boundaries $B_{GO}$ and $B_{OW}$. The volume of water is determined based upon the location of boundary $B_{OW}$ relative to bottom surface 158, the volume of oil is determined by the distance between boundaries $B_{GO}$ and $B_{OW}$ and the volume of gas is determined by the location of $B_{GO}$ relative to upper surface 156 or by subtraction.

The volume of the constituents on a percentage basis is calculated as:

$$\% \text{ Water} = \frac{V_{water}}{V_{total}} \quad \% \text{ Gas} = \frac{V_{gas}}{V_{total}} \quad \% \text{ Oil} = \frac{V_{oil}}{V_{total}}$$

Further sample characteristic analysis can be performed using transducer 400. Transducer 400 can be selected to measure the pressure of the sampled fluid within interior chamber 108. This pressure measurement can be, for example, used to determine the volume of gas in solution in the oil.

While this invention has been described with a reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A downhole apparatus for determining constituent composition of a produced fluid comprising:
    a vessel having an interior chamber for containing a sample of the produced fluid and allowing the sample of the produced fluid to separate into constituents; and
    a gauge having an array of transmitter elements and an array of receiver elements disposed oppositely of one another on the vessel, each transmitter element propagating an energy wave through the sample of the produced fluid that is received by the corresponding receiver element in the array of receiver elements such that the location of an interface between the constituents is identified, thereby determining the constituent composition of the produced fluid.

2. The apparatus as recited in claim 1 wherein the vessel has an inlet port and an outlet port in communication with a stream of the produced fluid.

3. The apparatus as recited in claim 2 further comprising a flow control device for selectively permitting and preventing the produced fluid from the stream of produced fluid from entering the interior chamber of the vessel through the inlet port.

4. The apparatus as recited in claim 2 further comprising a flow control device for selectively permitting and preventing the produced fluid from exiting the interior chamber of the vessel through the outlet port into the stream of produced fluid.

5. The apparatus as recited in claim 2 further comprising a flow control device having first and second positions, in the first position, the flow control device permitting the produced fluid from the stream of produced fluid to enter the interior chamber of the vessel through the inlet port and permitting the produced fluid to exit the interior chamber of the vessel through the outlet port into the stream of produced fluid, in the second position, the flow control device preventing the produced fluid from the stream of produced fluid from entering the interior chamber of the vessel through the inlet port and preventing the produced fluid from exiting the interior chamber of the vessel through the outlet port into the stream of produced fluids such that the interior chamber of the vessel is flushed and the sample of produced fluid is obtained.

6. The apparatus as recited in claim 1 wherein the portions of the vessel adjacent to the transmitter elements and the receiver elements are substantially transparent to the energy wave.

7. The apparatus as recited in claim 1 wherein each of the energy waves is a light wave.

8. The apparatus as recited in claim 1 wherein each receiver element detects changes in the energy wave transmitted from the corresponding transmitter element caused by the constituent of the sample of the produced fluid through which that energy wave propagated.

9. The apparatus as recited in claim 1 further comprising a pressure transducer.

10. The apparatus as recited in claim 1 further comprising a power source coupled to the gauge.

11. The apparatus as recited in claim 1 further comprising a data acquisition system coupled to the gauge.

12. The apparatus as recited in claim 1 wherein the gauge further comprises a transmitter and an array of receiver elements disposed oppositely of one another on the vessel.

13. A downhole apparatus for determining constituent composition of a produced fluid comprising:
 a vessel having an interior chamber for containing a sample of the produced fluid and allowing the sample of the produced fluid to separate into constituents; and
 a gauge having a transmitter and an array of receiver elements disposed oppositely of one another on the vessel, the transmitter propagating light energy through a lens that spreads the light energy into a plurality of light waves such that each receiver elements in the array of receiver elements receives one of the light waves that has traveled through the sample of the produced fluid such that the location of an interface between the constituents is identified, thereby determining the constituent composition of the produced fluid.

14. The apparatus as recited in claim 13 wherein at least one of the light waves travels through the interface between the constituents.

15. The apparatus as recited in claim 13 wherein the vessel has an inlet port and an outlet port in communication with a stream of the produced fluid.

16. The apparatus as recited in claim 15 further comprising a flow control device for selectively permitting and preventing the produced fluid from the stream of produced fluid from entering the interior chamber of the vessel through the inlet port.

17. The apparatus as recited in claim 15 further comprising a flow control device for selectively permitting and preventing the produced fluid from exiting the interior chamber of the vessel through the outlet port into the stream of produced fluid.

18. The apparatus as recited in claim 15 further comprising a flow control device having first and second positions, in the first position, the flow control device permitting the produced fluid from the stream of produced fluid to enter the interior chamber of the vessel through the inlet port and permitting the produced fluid to exit the interior chamber of the vessel through the outlet port into the stream of produced fluid, in the second position, the flow control device preventing the produced fluid from the stream of produced fluid from entering the interior chamber of the vessel through the inlet port and preventing the produced fluid from exiting the interior chamber of the vessel through the outlet port into the stream of produced fluids such that the interior chamber of the vessel is flushed and the sample of produced fluid is obtained.

19. A downhole method for determining constituent composition of a produced fluid comprising the steps of:
 disposing a fluid analyzing device having an interior chamber downhole;
 selectively communicating the interior chamber with a stream of the produced fluid;
 collecting a sample of the produced fluid in the interior chamber;
 allowing the produced fluid to separate into constituents;
 propagating energy waves through the sample of the produced fluid between corresponding transmitter elements and receiver elements of a gauge; and
 identifying the level of an interface between the constituents with the gauge, thereby determining the constituent composition of the produced fluid.

20. The method as recited in claim 19 wherein the step of selectively communicating the interior chamber with the stream of the produced fluid further comprises communicating an inlet port and an outlet port of the fluid analyzing device with the stream of the produced fluid.

21. The method as recited in claim 19 wherein the step of collecting the sample of the produced fluid in the interior chamber further comprises operating a flow control device to selectively permit and prevent the produced fluid from the stream of produced fluid to flow through the interior chamber of the fluid analyzing device.

22. The method as recited in claim 19 further comprising the step of flushing the interior chamber of the fluid analyzing device with the production fluid prior to the step of collecting the sample of the produced fluid in the interior chamber.

23. The method as recited in claim 19 wherein the energy waves are a light waves.

24. The method as recited in claim 19 further comprising detecting with the receiver elements the changes in the energy waves transmitted from the transmitter elements caused by the constituent of the sample of the produced fluid through which each energy wave propagated.

25. The method as recited in claim 19 further comprising measuring the pressure of the sample with a pressure transducer.

26. The method as recited in claim 19 further comprising transmitting data from the gauge to a data acquisition system.

27. A downhole method for determining constituent composition of a produced fluid comprising the steps of:
 disposing a fluid analyzing device having an interior chamber and a gauge downhole, the gauge comprising a transmitter and an array of receiver elements;
 selectively communicating the interior chamber with a stream of the produced fluid;
 collecting a sample of the produced fluid in the interior chamber;
 allowing the produced fluid to separate into constituents;
 propagating light energy from the transmitter through a lens to spread the light energy into a plurality of light waves and receiving one of the light waves that has traveled through the sample of the produced fluid with each of the receiver elements in the array of receiver elements; and identifying the level of an interface between the constituents with the gauge, thereby determining the constituent composition of the produced fluid.

28. The method as recited in claim 27 further comprising propagating at least one of the light waves through the interface between the constituents.

29. The method as recited in claim 27 further comprising detecting with the receiver elements the changes in the light energy transmitted from the transmitter caused by the constituent of the sample of the produced fluid through which each light wave propagated.

30. The method as recited in claim 27 further comprising transmitting data from the gauge to a data acquisition system.

* * * * *